US00RE42132E

(19) United States
(12) Reissued Patent
Hillisch et al.

(10) Patent Number: US RE42,132 E
(45) Date of Reissued Patent: Feb. 8, 2011

(54) ANTITUMORAL D-HOMOESTRA-1,3,5(10)-TRIEN-3-YL 2-SUBSTITUTED SULFAMATES

(75) Inventors: Alexander Hillisch, Solingen (DE); Olaf Peters, Tabarz (DE); Christian Gege, Ehingen (DE); Gerhard Siemeister, Berlin (DE); Eberhard Unger, Cospeda (DE); Bernd Menzenbach, Jena (DE)

(73) Assignee: Sterix Limited, Berkshire (GB)

(21) Appl. No.: 12/351,271

(22) PCT Filed: Feb. 19, 2004

(86) PCT No.: PCT/EP2004/001629

§ 371 (c)(1),
(2), (4) Date: Aug. 18, 2005

(87) PCT Pub. No.: WO2004/074309

PCT Pub. Date: Sep. 2, 2004

Related U.S. Patent Documents

Reissue of:
(64) Patent No.: 7,244,762
Issued: Jul. 17, 2007
Appl. No.: 10/546,230
Filed: Aug. 18, 2005

(30) Foreign Application Priority Data

Feb. 19, 2003 (DE) ..... 103 07 103

(51) Int. Cl.
*A61K 31/565* (2006.01)
*C07J 31/00* (2006.01)
*C07J 41/00* (2006.01)
*A61P 35/00* (2006.01)

(52) U.S. Cl. ..... 514/517; 558/48; 558/49
(58) Field of Classification Search ..... None
See application file for complete search history.

(56) References Cited

U.S. PATENT DOCUMENTS

| | | | | |
|---|---|---|---|---|
| 5,705,495 | A | 1/1998 | Schwarz | |
| 6,011,024 | A | 1/2000 | Reed et al. | |
| 6,046,186 | A | 4/2000 | Tanabe et al. | |
| 6,339,079 | B1 * | 1/2002 | Kasch et al. | 514/182 |
| 6,583,130 | B1 | 6/2003 | Schwarz et al. | |
| 6,903,084 | B2 | 6/2005 | Reed et al. | |
| 6,930,128 | B2 | 8/2005 | D'Amato et al. | |
| 7,244,762 | B2 | 7/2007 | Hillisch et al. | |
| 2002/0032180 | A1 | 3/2002 | Tanabe et al. | |
| 2002/0061868 | A1 | 5/2002 | Schwarz | |
| 2004/0127473 | A1 | 7/2004 | Reed et al. | |
| 2006/0160782 | A1 | 7/2006 | Hillisch et al. | |
| 2006/0211670 | A1 | 9/2006 | Hillisch et al. | |

FOREIGN PATENT DOCUMENTS

| | | |
|---|---|---|
| WO | WO 93/05064 | 3/1993 |
| WO | WO 96/05217 | 2/1996 |
| WO | WO 97/14712 | 4/1997 |
| WO | WO 98/24802 | 6/1998 |
| WO | WO-99 27935 | 6/1999 |
| WO | WO 99/33858 | 7/1999 |
| WO | WO 99/33859 | 7/1999 |
| WO | WO 99/64013 | 12/1999 |
| WO | WO 01/18028 | 3/2001 |
| WO | WO 01/30803 | 5/2001 |
| WO | WO 02/42319 | 5/2002 |

OTHER PUBLICATIONS

Organic Reactions, vol. 35, Andrew S. Kende (Editor–in–Chief), Chapter 3 by Milos Hudlicky, "Fluorination With Diethylaminosulfur Trifluoride And Related Aminofluorosulfuranes," pp. 513–637, May 1988.
Journal of Steroid Biochemistry & Molecular Biology 86 (2003) pp. 423–432—"Steriod sulphatase inhibitors for breast cancer therapy", A. Purohit et al.
Letters to Nature—Nature—vol. 368—Mar. 17, 1994—The endogenous oestrogen metabolite 2–methoxyoestradiol inhibits angiogenesis and suppresses tumour growth, Theodore Fotsis et al., pp. 237–239.
J. Med. Chem. 1995, vol. 38, pp. 2041–2049—Articles—"Synthesis, Antitubulin and Antimitotic Activity, and Cytotoxicity of Analogs of 2–Methoxyestradiol, an Endogenous Mammalian Metabolite of Estradiol That Inhibits Tubulin Polymerization by Binding to the Colchicine Binding Site", Mark Cushman et al.
J. Med. Chem. 1997, vol. 40, pp. 2323–2334—"Synthesis of Analogs of 2–Methoxyestradiol with Enhanced Inhibitory Effects on Tubulin Polymerization and Cancer Cell Growth", Mark Cushman et al.

(Continued)

*Primary Examiner*—Joseph K. McKane
*Assistant Examiner*—Michael Barker
(74) *Attorney, Agent, or Firm*—Millen, White, Zelano & Branigan, P.C.

(57) ABSTRACT

This invention relates to 2-substituted D-homo-estra-1,3,5(10)-trien-3-yl sulfamates of general formula I (I), in which R3 means a C1-C5-alkyl or C1-C5-alkyloxy group as well as their use for the production of a pharmaceutical agent for treating tumor diseases, which can be influenced positively by the inhibition of tubulin polymerization. The compounds according to the invention are distinguished by a D-homo-substitution. They have a special action with respect to tubulin polymerization inhibition and can be used, for example, for treating prostate cancer (I)

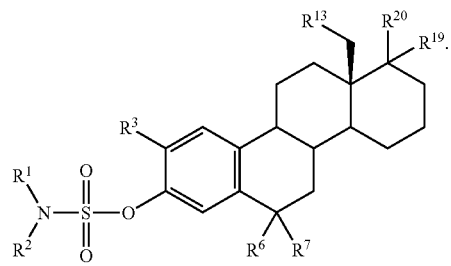

25 Claims, No Drawings

OTHER PUBLICATIONS

Cancer—Sep. 1, 2000, vol. 89, No. 5—"Comparison of 2–Methoxyestradiol–Induced, Docetaxel–Induced, and Paclitaxel–Induced Apoptosis in Hepatoma Cells and Its Correlation with Reactive Oxygen Species", Heng–Liang Lin et al., pp. 983–994.

Int. J. Cancer; 85, pp. 584–589 (2000)—"The Effect Of 2–Methoxyoestrone–3–O–Sulphamate On The Growth Of Breast Cancer Cells And Induced Mammary Tumours", Atul Purohit et al.

Elsevier—Molecular and Cellular Endocrinology 160 (2000) pp. 61–66—"Inhibition of deoxyglucose uptake in MCF–7 breast cancer cells by 2–methoxyestrone and 2–methoxyestrone–3–O–sulfamate", A. Singh et al.

Cancer Research 60, pp. 5441–5450, Oct. 1, 2000—XP 001031282—"Differential Effects of Estrone and Estrone–3–O–Sulfamate Derivatives on Mitotic Arrest, Apoptosis, and Microtubule Assembly in Human Breast Cancer Cells", Lucy MacCarthy–Morrogh et al.

Pergamon—Journal of Steroid Biochemistry and Molecular Biology 69 (1999) pp. 227–238—"Recent advances in the development of steroid sulphatase inhibitors", A. Purohit et al.

Chem. Pharm. Bull. vol. 18 (1970), pp. 474–480—"Studies on Steroid Conjugates. III. New Systheses of 2–Methoxyestrogens", Toshio Nambara et al.

Elsevier—Steroids 67 (2002) pp. 1065–1070—"A new, practical synthesis of 2–methoxyestradiols", Pemmaraju N. Rao et al.

Pahrmazie 56 (2001) 11—pp. 843–849—Original Articles—"Studies on modified estrogens: Towards the synthesis of novel 14,15–cyclopropa[a]estra–1,3,5(10), 8–tetraenes", S. Schwarz et al.

J. Med. Chem. 1989, vol. 32, pp. 1642–1652—"17–Desoxy Estrogen Analogues", Richard H. Peters et al.

Tetrahedron Letters No. 20, pp. 1823–1826—"A New Method For Fluorination Of Sterols", Shlomo Rozen et al. (1979).

Reports—Science, 286, pp. 531–537—(1999)—"Molecular Classification of Cancer: Class Discovery and Class Prediction by Gene Expression Monitoring", T.R. Golub et al.

Journal f. prakt. Chemie. Band 314, Heft 3–4, 1972, S. pp. 667–668—J.A. Barth, Leipzig—Steroide. XXXI [1]—"Ein vereinfachtes Verfahren zur Darstellung von Steroid–Spirooxiranen", Von M. Hubner et al.

Z. Chem. 22. Jg. (1982)—p. 186—"Zur Umseizung von vicinalen Steroidazidoalkoholen mit Triphenylphosphan"—Professor D. Gunther Drefahl.

Greene T. W., Wuts P. G.M., Protective Groups in Organic Synthesis, J. Wiley & Sons, 1999, S. pp. 273–278.

Welch J. T., Fluorine in Bloorganic Chemistry, 1991, John Wiley, New York.

Welch, J.T. (Fluorine in Bioorganic Chemistry),1991, 12,67, 148,201–202, John Wiley, New York.

* cited by examiner

ANTITUMORAL D-HOMOESTRA-1,3,5(10)-TRIEN-3-YL 2-SUBSTITUTED SULFAMATES

Matter enclosed in heavy brackets [ ] appears in the original patent but forms no part of this reissue specification; matter printed in italics indicates the additions made by reissue.

This invention relates to 2-substituted D-homoestra-1,3,5(10)-trien-3-yl sulfamates and their use for the production of pharmaceutical agents that have an antitumor-active activity.

Microtubuli are organelles that occur in most eukaryotic cells and take over a number of functions there such as mitosis, intracellular movements, cell migration and the manifestation of the cell shape. Microtubuli are polymers that consist of tubulin, which in turn represents a dimer that consists of an α-unit or a β-unit. These heterodimers bind two guanosine triphosphate (GTP) molecules, whereby one of the GTPs is securely bonded and the other is replaceable. In a head-tail arrangement, the heterodimers polymerize into thread-shaped macromolecules, the so-called protofilaments, which in turn pile up into tubular organelles, the microtubuli.

Microtubuli are subject to a constant build-up and degradation. The equilibrium between growth and degradation depends on the availability of new GTP-tubulin subunits and the rate of hydrolysis of the second bonded GTPs. On the plus end, new subunits are cultivated; conversely, on the minus end, subunits diffuse outward.

It is known that cytotoxic substances such as colchicine, vinblastine, vincristine, taxol, epothilone, podophyllotoxin, steganicin, combretastatin and 2-methoxyestradiol influence the build-up or degradation of microtubuli (tubulin polymerization and tubulin depolymerization) and thus are able to influence the cell division in a phase-specific manner. This relates primarily to quick-growing, neoplastic cells, whose growth is largely unaffected by intracellular regulating mechanisms. Active ingredients of this type are in principle suitable for treating malignant tumors.

Potsis et al. Nature 1994 368, 237-239 report, moreover, that 2-methoxyestradiol inhibits the tumor growth and the angiogenesis.

Cushman et al. J. Med. Chem. 1995 38, 2041-2049 examine the cytotoxic action as well as the tubulin-polymerization-inhibiting action of 2-methoxyestradiol, and report in J. Med. Chem. 1997, 40, 2323-2334, moreover, that 2-alkoxy-6-oximinoestradiol derivatives inhibit the tubulin polymerization as well as the bond of [$^3$H]-colchicine to tubulin. The 2-alkoxy-6-oximinoestradiol derivatives that are mentioned here show comparable activity, relative to the inhibition of tubulin polymerization, such as 2-ethoxyestradiol, which has a higher activity than 2-methoxyestradiol.

In contrast, steroid-3-sulfamates are described in the literature as inhibitors of steroid sulfatase:

WO 93/05064 relates to, i.a., compounds of formula

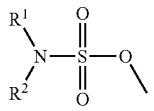

Polycyclic compound whereby $R^1$ and $R^2$, in each case independently of one another, mean hydrogen or a methyl group, provided that at least one of radicals $R^1$ and $R^2$ is an H atom, and the radical-O-polycyclic compound is a 3-sterol, whose sulfate ester can be hydrolyzed by an enzyme with steroid-sulfatase activity. Compounds that are substituted specifically in the 2-position of the steroid skeleton are not explicitly disclosed.

U.S. Pat. No. 6,011,024 is based on WO 93/05064 and covers, e.g., all compounds in which the primary sulfamate function is bonded to a six-membered ring. Compounds that are specifically substituted in the 2-position of the steroid skeleton are in turn not explicitly disclosed.

WO 96/05216 relates to C2-unsubstituted estra-1,3,5(10)-triene-sulfamate derivatives.

WO 96/05217 relates to pharmaceutical compositions that contain active ingredients of general formula

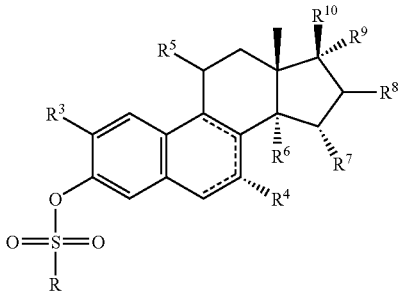

in which R=$NH_2$; $R^3$=$C_{1-5}$-alkoxy group, OH; $R^8$, $R^9$ and $R^{10}$, independently of one another, =H, OH; $R^9$ and $R^{10}$ together can have the meaning=0. The pharmaceutical compositions that are disclosed therein can be used for female birth control; menopausal HRT and for treatment of gynecological and andrological images of disease, such as breast cancer or prostate cancer.

WO 97/14712 relates to steroid sulfamate derivatives of general formula

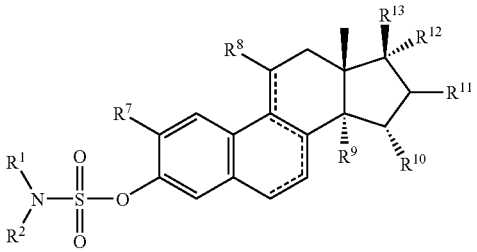

in which $R^1$ can represent an acyl, alkoxycarbonyl, aminocarbonyl, sulfonyl or sulfonamidyl group; $R^2$ can represent a hydrogen atom or a metal atom; $R^7$ and $R^8$, independently of one another, can represent H, OH and $C_{1-5}$-alkoxy; $F^{13}$, $R^{12}$ and $R^{11}$, independently of one another, can represent H or OH.

WO 98/42729 relates to 16-halogen-substituted 1,3,5-estratriene-3-monosulfamates as well as 3,17β-bissulfamates, which can be alkoxy-substituted at C2. The 16-halogen substitution increases both the sulfatase-inhibiting action and the estrogeneity of the corresponding sulfamate derivatives.

The introduction of a 17-sulfamate function in addition to the 3-sulfamate function drastically reduces the estrogeneity.

WO 98/24802 relates to sulfamates that inhibit the estrone sulfatase. 2-Methoxyestrone sulfamate is explicitly mentioned. As a potential therapeutic application, breast cancer, but not prostate cancer, is mentioned in the description.

Also, WO 99/33858 describes estrone sulfatase inhibitors of formula

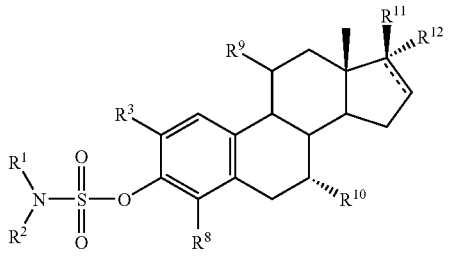

in which $R^1$ and $R^2$, independently of one another, represent H, alkyl, or together piperidine, morpholine, piperazine; $R^3$=H, CN, $NO_2$, $CO_2R^4$; $R^8$=H, $NO_2$, $NR^6R^7$. In the description, breast cancer is mentioned as a possible therapeutic application.

In WO 99/33859 as well as in US 2002/0032180, anti-estrogenic compounds are described that are suitable for treatment of different, primarily estrogen-dependent diseases. Preferred compounds have an estra-1,3,5(10)-triene building block and are substituted in 11-position and 17-position. Especially preferred are 17-deoxy-estra-1,3,5(10)-trienes. 2-Substituted D-homo-estra-1,3,5(10)-trien-3-yl sulfamates also fall under the general formulas, but corresponding compounds are not explicitly mentioned.

WO 99/64013 relates to a pharmaceutical composition of a sulfamate derivative with a cell signal modifier (such as, e.g., TNFα). 2-Methoxyestrone sulfamate is explicitly claimed as a preferred sulfamate in this combination; but numerous other steroid-3-sulfamates fall under the scope of the general formula. As a mechanism of action for the pharmaceutical compositions according to the invention or for the steroid-3-sulfamates contained therein (preferably with at least one 2-alkoxy substituent), 1) inhibition of the glucose absorption in tumor cells, 2) inhibition of tumor angiogenesies, 3) degradation of microtubuli; 4) inducing of apoptosis are described. WO 00/76487 relates to substances that inhibit the TNFα-induced aromatase activity. As such, 2-alkoxyestrone-3-sulfamates, preferably 2-methoxyestrone sulfamate, are claimed.

WO 01/18028 describes non-estrogenic estrone sulfatase-inhibiting N-acyl-18a-substituted steroid-3-sulfamates, such as, e.g., 16α-fluoro-2-methoxy-18a-homoestradiol-(N-acetylsulfamate) or 16α-fluoro-2-methoxy-18a-homoestrone-(N-acetylsulfamate).

In Cancer 2000, 85, 983-994, the 2-methoxyestradiol, docetaxel and paclitaxel-induced apoptosis in hepatoma cells and their correlation with reactive oxygen species are compared.

Potter et al. Int. J. Cancer 2000, 85, 584-589 examine the action of 2-methoxyestrone sulfamate in comparison to 2-methoxyestrone on the growth of breast cancer cells and induced breast tumors and find that 2-methoxyestrone sulfamate has a significant therapeutic potential for treating breast cancer.

Potter et al. Molecular and Cellular Endocrinology 2000, 160, 61-66 examine the inhibition of deoxyglucose absorption in MCF-7 breast cancer cells by 2-methoxyestrone and 2-methoxyestrone-3-sulfamate, which inhibit glucose absorption by 25 to 49% with 10 μm (also 2-methoxyestradiol and 2-methoxyestrone), and it follows that the compounds could have therapeutic potential for inhibiting breast cancer by their capacity to inhibit glucose absorption.

Potter et al. Cancer Research 2000, 60, 5441-5450 describe 2-methoxyestrone-sulfamate and 2-ethoxyestrone sulfamate as new antimicrotubulin-active compounds that have in-vitro anti-cancer activity in breast cancer cells and therefore also optionally could be active in vivo. In J. Steroid Biochem. Mol. Biol. 1999, 69, 227-238, it is reported that the inhibition of the steroid sulfatase activity is an important starting point in the treatment of hormone-dependent breast cancer. 2-Methoxyestrone sulfamate, 17-deoxyestrone sulfamate and estrone sulfamate are cited explicitly. Monocyclic or bicyclic, non-steroidal sulfamates namely inhibit the steroid sulfatase, but not as effectively as the corresponding steroid derivatives.

The object of this invention consists in making available additional compounds that effectively inhibit tubulin polymerization.

The object of this invention is achieved according to the invention by the provision of 2-substituted D-homoestra-1,3,5(10)-trien-3-yl sulfamates of general formula I:

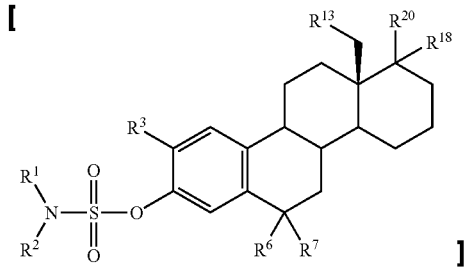

(I)

in which $R^1$ and $R^2$, independently of one another, mean a hydrogen atom, a methyl group, a $C_1$-$C_4$-acyl group or a benzoyl group, $R^3$ means a $C_1$-$C_5$-alkyl, a $C_1$-$C_5$-alkyloxy group or a radical —O—$C_nF_mH_o$, whereby n=1, 2, 3, 4, 5 or 6, m>1, and m+o=2n+1, $R^6$ and $R^7$, independently of one another, mean a hydrogen atom, a hydroxy group, an amino group or an NHR group, whereby $R^8$ is an acetyl group, or $R^6$ and $R^7$ together are an oxime NOH, $R^{13}$ is a hydrogen atom or a methyl group, $R^{19}$ is a hydrogen atom or a fluorine atom, $R^{20}$ is a hydrogen atom or a fluorine atom or a hydroxy group or a $C_1$-$C_5$-alkyloxy group or a $C_1$-$C_5$-alkyl group or a radical —$C_nF_mH_o$, whereby n=1, 2, 3, 4, 5 or 6, m>1 and m+o=2n+1 or a group $SO_2NR^1R^2$, $R^{19}$ and $R^{20}$ together mean an oxygen atom, a methylene group, a difluoromethylene group or a monofluoromethylene group or an oxime $NOR^{21}$, whereby $R^{21}$ is a hydrogen atom or a $C_1$-$C_5$-alkyl group, as well as their pharmaceutically acceptable salts.

In addition, this invention comprises the new compounds as pharmaceutical active ingredients, their production, their therapeutic application and the pharmaceutical dispensing forms that contain the new substances.

The compounds of general formula (I) according to the invention or their pharmaceutically acceptable salts can be used for the production of a pharmaceutical agent, especially for treating tumor diseases that can be influenced positively by the inhibition of tubulin polymerization.

It was determined that the 2-substituted D-homoestra-1,3,5(10)-trien-3-yl sulfamates according to the invention more greatly inhibit in vitro the tubulin polymerization, surprisingly enough, than 2-methoxyestradiol. The compounds according to the invention inhibit the proliferation of tumor cells and also show in-vivo antitumor action.

In addition, the compounds according to the invention have better oral bioavailability than 2-methoxyestradiol.

The $C_1$-$C_5$-alkyl groups for $R^3$ or $R^{20}$ can readily be a methyl, ethyl, n-propyl, iso-propyl; n-, iso- or tert-butyl; n-, iso- or neo-pentyl group.

A formyl, acetyl, propionyl, butyryl, or iso-butyryl radical can stand for an acyl radical $R^1$ and $R^2$.

A methoxy, ethoxy, n-propoxy, iso-propoxy; n-, iso-, or tert-butoxy; n-, iso- or neo-pentoxy group can stand for the $C_1$-$C_5$-alkoxy radical $R^3$ or $R^{20}$.

Preferred according to this invention are compounds of general formula I, in which:

$R^1$ represents H, methyl, acetyl, propionyl, butyryl, in particular H, $R^2$ represents H, acyl, $R^3$ represents methyl, ethyl, methoxy, 2,2,2-trifluoroethoxy, $R^6$ and $R^7$ both represent hydrogen or together oxime, $R^{13}$ represents H or methyl, $R^{19}$ represents H, $R^{20}$ represents H, OH, $C_1$-$C_5$-alkyloxy, in particular H, OH, The compounds mentioned below as well as their use are especially preferred according to the invention:

1) 2-Methoxy-17a-oxo-17a-homoestra-1,3,5(10)-trien-3-yl sulfamate (1)
2) 2-Methoxy-17a-oxo-17a-homoestra-1,3,5(10)-trien-3-yl (N-acetyl)-sulfamate
3) 2-Methoxy-17a-homoestra-1,3,5(10)-trien-3-yl sulfamate (2)
4) 2-Methoxy-17a-homoestra-1,3,5(10)-trien-3-yl (N-acetyl)-sulfamate
5) 2-Methoxy-6-oximino-17a-homoestra-1,3,5(10)-trien-3-yl sulfamate
6) 2-Methoxy-6-(O-methyloximino)-17a-homoestra-1,3,5(10)-trien-3-yl sulfamate
7) 6α-Hydroxy-2-methoxy-17a-homoestra-1,3,5(10)-trien-3-yl sulfamate
8) 6α-Acetylamino-2-methoxy-17a-homoestra-1,3,5(10)-trien-3-yl sulfamate
9) 2-Methoxy-6-oxo-17a-homoestra-1,3,5(10)-trien-3-yl sulfamate
10) 17aα-Hydroxy-2-methoxy-17a-homoestra-1,3,5(10)-trien-3-yl sulfamate (3a)
11) 17aβ-Hydroxy-2-methoxy-17a-homoestra-1,3,5(10)-trien-3-yl sulfamate (3b)
12) 2-Methoxy-17a-homoestra-1,3,5(10)-triene-3,17aβ-diyl bissulfamate (4)
13) 2-Methoxy-17a-homoestra-1,3,5(10)-triene-3,17aβ-diyl bis-(N-acetyl)-sulfamate
14) 17a-Difluoro-2-methoxy-17a-homoestra-1,3,5(10)-trien-3-yl sulfamate
15) 17aα-Fluoro-2-methoxy-17a-homoestra-1,3,5(10)-trien-3-yl sulfamate
16) 17aβ-Fluoro-2-methoxy-17a-homoestra-1,3,5(10)-trien-3-yl sulfamate
17) 2-Methoxy-17a-oximino-17a-homoestra-1,3,5(10)-trien-3-yl sulfamate
18) 2-Methoxy-17a-(methyloximino)-17a-homoestra-1,3,5(10)-trien-3-yl sulfamate
19) 2,17aβ-Dimethoxy-17a-homoestra-1,3,5(10)-trien-3-yl sulfamate
20) 2,17aβ-Dimethoxy-17a-homoestra-1,3,5(10)-trien-3-yl (N-acetyl)-sulfamate
21) 17aβ-Ethoxy-2-methoxy-17a-homoestra-1,3,5(10)-trien-3-yl sulfamate
22) 17aβ-Ethoxy-2-methoxy-17a-homoestra-1,3,5(10)-trien-3-yl (N-acetyl)-sulfamate
23) 2-Methoxy-17aβ-(n-propoxy)-17a-homoestra-1,3,5(10)-trien-3-yl sulfamate
24) 2-Methoxy-17aβ-methyl-17a-homoestra-1,3,5(10)-trien-3-yl sulfamate
25) 17aβ-Difluoromethyl-2-methoxy-17a-homoestra-1,3,5(10)-trien-3-yl sulfamate
26) 17aβ-Fluoromethyl-2-methoxy-17a-homoestra-1,3,5(10)-trien-3-yl sulfamate
27) 17aβ-Ethyl-2-methoxy-17a-homoestra-1,3,5(10)-trien-3-yl sulfamate
28) 2-Methoxy-17a(20)-methylene-17a-homoestra-1,3,5(10)-trien-3-yl sulfamate
29) 17a(20)-Difluoromethylene-2-methoxy-17a-homoestra-1,3,5(10)-trien-3-yl sulfamate
30) 17a(20)-Fluoromethylene-2-methoxy-17a-homoestra-1,3,5(10)-trien-3-yl sulfamate
31) 2-Methoxy-17a-oxo-17a,18a-dihomoestra-1,3,5(10)-trien-3-yl sulfamate
32) 2-Methoxy-17a-oxo-17a,18a-dihomoestra-1,3,5(10)-trien-3-yl (N-acetyl)-sulfamate
33) 2-Methoxy-17a,18a-dihomoestra-1,3,5(10)-trien-3-yl sulfamate
34) 2-Methoxy-17a,18a-dihomoestra-1,3,5(10)-trien-3-yl (N-acetyl)-sulfamate
35) 2-Methoxy-6-oximino-17a,18a-dihomoestra-1,3,5(10)-trien-3-yl sulfamate
36) 2-Methoxy-6-(O-methyloximino)-17a,18a-dihomoestra-1,3,5(10)-trien-3-yl sulfamate
37) 6α-Hydroxy-2-methoxy-17a,18a-dihomoestra-1,3,5(10)-trien-3-yl sulfamate
38) 6α-Acetylamino-2-methoxy-17a,18a-dihomoestra-1,3,5(10)-trien-3-yl sulfamate
39) 17aβ-Hydroxy-2-methoxy-17a,18a-dihomoestra-1,3,5(10)-trien-3-yl sulfamate
40) 2-Methoxy-17a,18a-dihomoestra-1,3,5(10)-triene-3,17aβ-diyl bissulfamate
41) 2-Methoxy-17a,18a-dihomoestra-1,3,5(10)-triene-3,17aβ-diyl bis-(N-acetyl)-sulfamate
42) 17a-Difluoro-2-methoxy-17a,18a-dihomoestra-1,3,5(10)-trien-3-yl sulfamate
43) 17aα-Fluoro-2-methoxy-17a,18a-dihomoestra-1,3,5(10)-trien-3-yl sulfamate
44) 17aβ-Fluoro-2-methoxy-17a,18a-dihomoestra-1,3,5(10)-trien-3-yl sulfamate 45) 2-Methoxy-17a-oximino-17a,18a-dihomoestra-1,3,5(10)-trien-3-yl sulfamate 46) 2-Methoxy-17a-(methyloximino)-17a,18a-dihomoestra-1,3,5(10)-trien-3-yl sulfamate 47) 2,17aβ-Dimethoxy-17a,18a-dihomoestra-1,3,5(10)-trien-3-yl sulfamate 48) 17aβ-Ethoxy-2-methoxy-17a,18a-dihomoestra-1,3,5(10)-trien-3-yl sulfamate 49) 2-Methoxy-17aβ-(n-propoxy)-17a,18a-dihomoestra-1,3,5(10)-trien-3-yl sulfamate 50) 2-Methoxy-17aβ-methyl-17a,18a-dihomoestra-1,3,5(10)-trien-3-yl sulfamate 51) 17aβ-Difluoromethyl-2-methoxy-17a,18a-dihomoestra-1,3,5(10)-trien-3-yl sulfamate 52) 17aβ-Fluoromethyl-2-methoxy-17a,18a-dihomoestra-1,3,5(10)-trien-3-yl sulfamate 53) 17aβ-Ethyl-2-methoxy-17a,18a-dihomoestra-1,3,5(10)-trien-3-yl sulfamate 54) 2-Methoxy-17a(20)-methylene-17a,18a-dihomoestra-1,3,5(10)-trien-3-yl sulfamate 55) 17a(20)-Difluoromethylene-2-methoxy-17a,18a-dihomoestra-1,3,5(10)-trien-3-yl sulfamate 56) 17a(20)-Fluoromethylene-2-methoxy-17a,18a-dihomoestra-1,3,5(10)-trien-3-yl sulfamate 57) 2-Ethyl-17a-oxo-17a-homoestra-1,3,5(10)-trien-3-yl sulfamate 58) 2-Ethyl-17a-oxo-17a-homoestra-1,3,5(10)-trien-3-yl (N-acetyl)-sulfamate 59) 2-Ethyl-17a-homoestra-1,3,5(10)-trien-3-yl sulfamate 60) 2-Ethyl-17a-homoestra-1,3,5(10)-trien-3-yl (N-acetyl)-sulfamate 61) 2-Ethyl-17aβ-hydroxy-17a-homoestra-1,3,5(10)-trien-3-yl sulfamate 62) 2-Ethyl-17a-homoestra-1,3,5(10)-triene-3,17aβ-diyl bissulfamate 63) 2-Ethyl-17a-homoestra-1,3,5(10)-triene-3,17aβ-diyl bis-(N-acetyl)-sulfamate 64) 2-Ethyl-17aβ-methoxy-17a-homoestra-1,3,5(10)-trien-3-yl sulfamate 65) 2-Ethyl-17aβ-ethoxy-17a-homoestra-1,3,5(10)-trien-3-yl sulfamate Pharmacological Data 1. Inhibition of Tubulin Polymerization The compounds according to the invention were tested in various models.

The compounds of general formula I according to the invention are distinguished in that they more greatly inhibit tubulin polymerization than 2-methoxyestradiol. The in-vitro testing of the tubulin polymerization influence was performed as follows:

According to Shelanski et al. (Shelanski et al. Proc. Natl. Acad. Sci. USA 1973, 70, 765-8), microtubular protein was purified from pig brains via cydic assembling/disassembling. The buffer system used had the following composition: 20 mmol of PIPES (1,4-piperazine-diethanesulfonic acid, pKa 6.8), 80 mmol of NaCl, 0.5 mmol of $MgCl_2$, 1 mmol of EGTA [ethylene glycol-bis-(2-aminoethylene)-tetraacetic acid].

For active ingredient testing, protein concentrations of 1 mg/ml (about $10^{-5}$ mmol of tubulin) were used. The determination of protein was carried out according to the Lowry Method (Lowry et al. J. Biol. Chem. 1951, 193, 265-75) with bovine serum albumin as a standard. The assembling of microtubuli was carried out in the presence of 0.25 mmol of GTP and heating the samples to 37° C.

The microtubulus formation was examined by means of turbidimetry at a wavelength of 340 nm. The state of equilibrium, in which the microtubular protein exhibits no increase in the assemblate concentration (corresponding to the microtubulus concentration) and the turbidity value no longer exhibits an increase, is typically reached after 20 minutes.

Testing of the active ingredients was carried out by their addition at the beginning of the assembling or in the state of equilibrium. Deviations of turbidity curves from the control characterize its activity. To monitor action and to evaluate the measured turbidity values, a transmission electron microscopic study (CEM 902 A, Zeiss/Oberkochen) of the assemblates was always performed after negative staining with 1% aqueous uranyl acetate.

TABLE 1

| Compound | Inhibition of Tubulin Polymerization $IC_{50}$ [μm] |
|---|---|
| 2-Methoxyestradiol | 2.7 |
| (2) | 0.95 |

2. Inhibition of Cell Proliferation

The compounds according to the invention are distinguished by a potent inhibition of cell proliferation.

Cell cultures of the following cell lines were prepared in 96-well microtiter plates:

1. MaTu/ADR multidrug-resistant human breast tumor cells (Epo GmbH Berlin), 5000 cells/well.
2. HCT116 human colon tumor cells (ATCC CCL-247), 3000 cells/well.
3. NCl-H460 human non-small-cell lung cancer cells (ATCC HTB-177), 3000 cells/well.
4. DU145 human prostate tumor cells (ATCC HTB-81), 5000 cells/well.
5. HMVEC human primary dermal microvascular endothelial cells, 7500 cells/well.

After 24 hours of incubation in a cell culture incubator at 37° C., the cells of a microtiter plate were stained with crystal violet (reference plate), while the cells in the test plates were incubated for 4 days with the test substances in the concentrations 0.1-10 μm, as well as with the DMSO solvent by itself (solvent control). The cell proliferation was determined by staining cells with crystal violet. The extinction of the crystal violet was determined by photometry at 595 nm. The percentage of the change in the cell number in the test plates was determined after the extinction values were normalized to the reference plate (0%) and to the solvent control (100%). The semi-maximal inhibition of the cell growth (IC50) was determined as the substance concentration, in which 50% of the cell number of the solvent controls were present.

TABLE 2

| | Inhibition of Cell Proliferation IC50 [μm] | | | | |
|---|---|---|---|---|---|
| Compound | NCI-H460 | HCT116 | DU145 | MaTu/ADR | HMVEC |
| Taxol | 0.004 | 0.004 | 0.004 | 0.4 | 0.004 |
| 2-Methoxy-estradiol | 1.8 | 1.1 | 1.9 | 0.2 | 2.2 |
| (1) | 0.18 | 0.18 | 0.5 | 0.1 | 0.22 |
| (2) | 0.6 | 0.6 | 0.6 | 0.2 | 0.5 |
| (4) | 1.8 | 1.8 | 2.8 | 0.8 | 0.6 |

Dosage

In general, satisfactory results can be expected when the daily doses comprise a range of 5 μg to 50 mg of the compound according to the invention per kg of body weight. In larger mammals, for example in humans, a recommended daily dose is in the range of 10 μg to 30 mg per kg of body weight.

Suitable dosages for the compounds according to the invention are from 0.005 to 50 mg per day per kg of body weight, depending on the age and constitution of the patient, whereby the necessary daily dose can be administered one or more times.

Based on the special depot action of the estrogen-sulfamates, the compounds according to the invention can, however, also be administered at greater intervals than once per day.

The formulation of the pharmaceutical preparations based on the new compounds is carried out in a way that is known in the art, by the active ingredient being processed with the vehicles, fillers, substances that influence decomposition, binding agents, moisturizing agents, lubricants, absorbing agents, diluents, flavoring correctives, coloring agents, etc., that are commonly used in galenicals and converted into the desired form of administration. In this case, reference is made to Remington's Pharmaceutical Science, 15$^{th}$ Edition, Mack Publishing Company, East Pennsylvania (1980).

For oral administration, in particular tablets, coated tablets, capsules, pills, powders, granulates, lozenges, suspensions, emulsions or solutions are suitable.

For parenteral administration, injection and infusion preparations are possible.

For intraarticular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local therapy.

For pulmonary administration of the new compounds, the latter can be used in the form of aerosols and inhalants.

For topical application, formulations in gels, ointments, fatty ointments, creams, pastes, powders, milks and tinctures are possible. The dosage of the compounds of general formula I should be 0.01%-20% in these preparations to achieve an adequate pharmacological action.

This invention comprises the compounds of general formula I and their use for the production of a pharmaceutical agent, in particular for treating tumor diseases that can be influenced positively by the inhibition of tubulin polymerization.

The compounds of general formula I according to the invention are preferably used for the production of a pharmaceutical agent, in particular for treating tumor diseases of the male and female gonads, male and female sex organs including the mammary glands, in particular of prostate cancer or breast cancer.

This invention also relates to pharmaceutical compositions that contain at least one especially preferred compound according to the invention, optionally in the form of a pharmaceutically/pharmacologically compatible salt, without or together with pharmaceutically compatible adjuvants and/or vehicles.

These pharmaceutical compositions and pharmaceutical agents can be provided for oral, rectal, vaginal, subcutaneous, percutaneous, intravenous or intramuscular administration. In addition to commonly used vehicles and/or diluents, they contain at least one especially preferred compound according to the invention.

The pharmaceutical agents of the invention are produced with commonly used solid or liquid vehicles or diluents and the commonly used pharmaceutical-technical adjuvants corresponding to the desired type of administration at a suitable dosage in a known way. The preferred preparations consist in a dispensing form that is suitable for oral administration. Such dispensing forms are, for example, tablets, film tablets, coated tablets, capsules, pills, powders, solutions or suspensions or else depot forms.

The pharmaceutical compositions that contain at least one of the compounds according to the invention are preferably administered orally.

Parenteral preparations such as injection solutions are also considered. In addition, for example, suppositories and agents for vaginal application can also be mentioned as preparations.

Corresponding tablets can be obtained by, for example, mixing active ingredient with known adjuvants, for example inert diluents such as dextrose, sugar, sorbitol, mannitol, polyvinyl pyrrolidone, explosives such as corn starch or alginic acid, binding agents such as starch or gelatin, lubricants such as magnesium stearate or talc and/or agents for achieving a depot effect such as carboxyl polymethylene, carboxylmethyl cellulose, cellulose acetate phthalate or polyvinyl acetate. The tablets can also consist of several layers.

Coated tablets accordingly can be produced by coating cores, which are produced analogously to the tablets, with agents that are commonly used in tablet coatings, for example, polyvinyl pyrrolidone or shellac, gum Arabic, talc, titanium oxide, or sugar. In this case, the shell of the coated tablets can also consist of several layers, whereby the adjuvants that are mentioned above in the tablets can be used.

Solutions or suspensions with the compounds of general formula I according to the invention can contain additional taste-improving agents such as saccharine, cyclamate or sugar, as well as, e.g., flavoring substances such as vanilla or orange extract. In addition, they can contain suspending adjuvants such as sodium carboxy methyl cellulose or preservatives such as p-hydroxybenzoates.

Capsules that contain the compounds of general formula I can be produced by, for example, the compound(s) of general formula I being mixed with an inert vehicle such as lactose or sorbitol and encapsulated in gelatin capsules, Suitable suppositories can be produced by, for example, mixing with vehicles that are provided for this purpose, such as neutral fats or polyethylene glycol or derivatives thereof.

For therapy of prostate cancer, the compounds according to the invention can be administered in combination with one or more of the following active ingredients:

1) Antiandrogens such as CPA, flutamide, casodex, etc.
2) Gonadotrophic hormone (GnRH) agonists
3) 5α-Reductase inhibitors such as finasteride
4) Cytostatic agents
5) VEGF-kinase inhibitors
6) Antigestagens
7) Antiestrogens
8) Antisense oligonucleotides
9) EGF antibodies
10) Estrogens Moreover, the compounds of general formula I according to the invention can be used for therapy and prophylaxis of other pathologic conditions that are not mentioned above.

The compounds of general formula I according to the invention can be produced as described below:

The functionalization of C-atom 2 of an estra-1,3,5(10)-trien-17-one derivative is preferably carried out by Friedel- Crafts acylation as described in the literature (T. Nambara et al. Chem. Pharm. Bull. 1979, 18, 474-480).

After changing the protective group in 3-position, a 2-carboxy-estra-1,3,5(10)-trien-17-one is generated by Baeyer-Villiger oxidation (M. B. Smith, J. March, March's Advanced Organic Chemistry, $5^{th}$ Edition, Wiley Sons 2001, 1417-1418 and literature cited there). The ester is saponified and converted with the corresponding alkyl halide under basic conditions into a 2-alkyl ether. Alternately, the 17-ketone as known can now be reduced and etherified. The cleavage of the protective group in 3-position is carried out as described in the literature (T. W. Greene, P. G. M. Wuts, Protective Groups in Organic Synthesis, Wiley & Sons, 1999, 249-275). This process or other processes known from the literature (P. N. Rao, J. W. Cessac, Steroids 2002, 67, 1065-1070 and literature cited there) can be used according to the 17a-homo or 17a,18a-dihomo derivatives.

The 2-acyl derivatives that are preferably obtained by Friedel-Crafts acylation can be converted by reduction with sodium borohydride and subsequent hydrogenation into the corresponding 2-alkyl derivatives.

The corresponding 17a-oxime, 17a-alkylene (so-called Wittig reaction, see, e.g., S. Schwarz et al. Pkarmazie 2001, 56, 843-849), 17a-difluoromethylene (Wadsworth-Emmons Reaction, S. R. Piettre, L. Cabanas, Tetrahedron Lett. 1996, 37, 5881-4884), and 17α,β-alkyl derivatives can also be produced from the 2-functionalized derivatives (e.g., R. H. Peters et al., J. Med. Chem. 1989, 32, 1642; G. E. Agoston et al. WO 02/42319) and then are sulfamoylated in 3-position.

According to Cushman et al (J. Med. Chem. 1997, 40, 2323), the synthesis of 6-functionalized estrogen derivatives is carried out by oxidation of the acetyl-protected estrogen derivative with chromium trioxide.

Starting from the 2-functionalized 17-keto derivatives, 17-oxiranes (M. Hübner, I. Noack, J. prakt. Chem. 1972, 314, 667) and from them the corresponding 17a-homo derivatives (M. Hübner, K. Ponsold, Z. Chem. 1982, 22, 186) can be produced.

17a-Fluorinated derivatives can be produced from the corresponding 17a-oxo or 17a-hydroxy derivatives with diethylamino-sulfur trifluoride (M. Hudlicky, Org. Reactions 1988, 35, 513; J. T. Welch, Fluorine in Bioorganic Chemistry 1991, John Wiley, New York; S, Rozen et al. Tetrahedron Lett. 1979, 20, 1823-1826) and then sulfamoylated.

This invention is explained in more detail based on the examples below, without being limited thereto:

PRODUCTION PROCESS

General Instructions 1 for the Production of 17a-Homoestra-1,3,5(10)-trien-3-yl Sulfamates One equivalent of a 17a-homoestra-1,3,5(10)-triene derivative in methylene chloride is dissolved or suspended while being stirred and mixed with 5 equivalents of 2,6-di-tert-butylpyridine. Then, 10 equivalents of sulfamoyl chloride are added under argon and stirred at room temperature. The solution is stirred until conversion Is completed (TLC monitoring, 1-5 hours) and then mixed with water. In acid-sensitive compounds, buffering is done in advance with about 10 equivalents of trimethylamine. The aqueous phase is extracted several times with dichloromethane or ethyl acetate. The combined organic phases are dried on sodium sulfate and concentrated by evaporation in a vacuum and then purified by flash chromatography.

General Synthesis Instructions 2 for Acylation of Sulfamates

One equivalent of the 17a-homoestra-1,3,5(10)-triene-sulfamate or bissulfamate is dissolved in pyridine and mixed with 5 equivalents of anhydride while being cooled with ice (0 to 5° C.). Stirring is continued for 1 hour at room temperature and then mixed with water. The aqueous phase is extracted several times with dichloromethane or ethyl acetate. The combined organic phases are washed with 6N hydrochloric acid and then with water and sodium chloride solution. Then, it is dried on sodium sulfate and concentrated by evaporation in a vacuum and then purified by flash chromatography.

The following compounds according to the invention were produced according to the above-mentioned instructions:

EXAMPLE 1

2-Methoxy-17a-oxo-17a-homoestra-1,3,5(10)-trien-3-yl Sulfamate (1)

3.61 g of 17α-azidomethyl-3,17β-dihydroxy-2-methoxyestra-1,3,5(10)-triene and 7.5 g of sodium iodide were suspended in 250 ml of acetonitrile and mixed slowly at room temperature with 15 ml of trimethylsilyl chloride. After 4 hours, another 4 ml of trimethylsilyl chloride was added, and after another 2.5 hours, it was mixed with saturated sodium thiosulfate solution and water and extracted with dichloromethane (3×). The combined organic phases were washed with aqueous sodium bicarbonate solution, dried and concentrated by evaporation in a rotary evaporator. Flash chromatography (cyclohexane/ethyl acetate= 10:1→7:1→5:1) yielded 2.12 g (67%) of 3-hydroxy-2-methoxy-17a-oxo-17a-homoestra-1,3,5(10)-triene as colorless crystals.

$^1$H-NMR($CDCl_3$): δ=1.13 (s, 3H: 18-$CH_3$), 2.62-2.71 (m, 1H: 17-H), 2.77 (dd, 2H: 6-$CH_2$), 3.86 (s, 3H; 2-$OCH_3$), 5.48 (s, 1H; 3-OH), 6.63, 6.78 (2 s, 2H; 1-H, 4-H).

492 mg of 3-hydroxy-2-methoxy-17a-oxo-17a-homoestra-1,3,5(10)-triene were reacted to form the product according to the general synthesis instructions and then purified by flash chromatography (cyclohexane/ethyl acetate= 3:1→2:1). 545 mg (89%) of 2-methoxy-17a-oxo-17a-homoestra-1,3,5(10)-trien-3-yl sulfamate (1) was obtained as colorless crystals.

$^1$H-NMR ($CDCl_3$): δ=1.13 (s, 3H; 18-$CH_3$), 2.63-2.71 (m, 1H; 17-H), 2.74-2.84 (m, 2H; 6-$CH_2$), 3.88 (s, 3H; 2-$OCH_3$), 5.00 (s, 2H; $NH_2$), 6.93, 7.04 (2 s, 2H; 1-H, 4-H).

EXAMPLE 2

2-Methoxy-17a-homoestra-1,3,5(10)-trien-3-yl Sulfamate (2)

600 mg of 3-hydroxy-2-methoxy-17a-oxo-17a-homoestra-1,3,5(10)-triene was dissolved in 20 ml of triethylene glycol and mixed under argon with 15 ml of hydrazine-monohydrate and 0.8 g of potassium hydroxide. Then, it was heated for 2 hours to 130° C. and then for another 1.5 hours to 200° C. After cooling to room temperature, it was acidified with 6N hydrochloric acid and extracted with dichloromethane (3×). The combined organic phases were washed with saturated sodium bicarbonate solution, dried and concentrated by evaporation in a rotary evaporator. Flash chromatography (cyclohexane/ethyl acetate=100: 1→50:1→20:1) yielded 541 mg (94%) of 3-hydroxy-2-methoxy-17a-homoestra-1,3,5(10)-triene as colorless crystals.

$^1$H-NMR ($CDCl_3$): δ=0.85 (s, 3H; 18-$CH_3$), 2.71-2.74 (m, 2H; 6-$CH_2$), 3.85 (s, 3H; 2-$OCH_3$); 5.41 (s, 1H: 3-OH), 6.62, 6.79 (2 s, 2H; 1-H, 4-H).

253 mg of 3-hydroxy-2-methoxy-17a-homoestra-1,3,5(10)triene was reacted to form the product according to general synthesis instructions 1 and then purified by flash chromatography (toluene/ethyl acetate=20:1→10:1). 217 mg (68%) of 2-methoxy-17a-homoestra-1,3,5(10)-trien-3-yl sulfamate (2) was obtained in the form of colorless crystals.

$^1$H-NMR ($CDCl_3$): δ=0.85 (s, 3H; 18-$CH_3$), 2.67-2.82 9m, 2H: 6-$CH_2$), 3.86 (s, 3H: 2-$OCH_3$), 4.97 (s, 2H: $NH_2$), 6.93, 7.02 (2 s, 2H; 1-H, 4-H).

EXAMPLE 3

17aα-Hydroxy-2-methoxy-17a-homoestra-1,3,5(10)-trien-3-yl Sulfamate (3a) and 17aβ-Hydroxy-2-methoxy-17a-homoestra-1,3,5(10)-trien-3-yl Sulfamate (3b)

298 mg of 2-methoxy-17a-oxo-17a-homoestra-1,3,5(10)-trien-3-yl sulfamate (2) was dissolved in 20 ml of methanol and 10 ml of tetrahydrofuran and mixed with 115 mg of sodium borohydride while being cooled with ice. After 2 hours, it was mixed with acetone and concentrated by evaporation in a rotary evaporator. The residue was acidified with 6N hydrochloric acid and extracted with dichloromethane (2×). The combined organic phases were washed with saturated sodium bicarbonate solution, dried and concentrated by evaporation in a rotary evaporator. Flash chromatography (n-hexane/ethyl acetate=3.2→1:1) yielded 35 mg (12%) of the α-epimer 3a as well as 276 mg (92%) of the β-epimer 3b as amorphous solids.

3a: $^1$H-NMR ($CDCl_3$): δ=0.86 (s, 3H; 18-$CH_3$), 3.42 (dd, $^3J_{eq}$=$^3J_{ax}$=2.7 Hz, 1H; 17aβ-H), 3.86 (s, 3H; 2-$OCH_3$), 5.14 (s, 2H; $NH_2$), 6.92, 7.02 (2 s, 2H; 1-H, 4-H).

3b: $^1$H-NMR ($CDCl_3$): δ=0.84 (s, 3H; 18-$CH_3$), 3.25 (dd, $^3$J=4.3 and 11.3 Hz, 1H; 17aα-H), 3.87 (s, 3H; 2-$OCH_3$), 5.07 (s, 2H; $NH_2$), 5.29 (s, 1H; OH), 6.93, 7.03 (2 s, 2H; 1-H, 4-H).

EXAMPLE 4

2-Methoxy-17a-homoestra-1,3,5(10)-triene-3,17aβ-diyl Bissulfamate (4)

62 mg of 17aβ-hydroxy-2-methoxy-17a-homoestra-1,3,5(10)-trien-3-yl sulfamate (3b) was reacted to form the product according to general synthesis instructions and then purified by flash chromatography (toluene/ethyl acetate=3:1). 55 mg (74%) of 2-methoxy-17a-homoestra-1,3,5(10)-triene-3,17aβ-diyl bissulfamate (4) was obtained as colorless oil, which slowly crystallized.

$^1$H-NMR (DMSO-$d_6$): δ=0.84 (s, 3H; 18-$CH_3$), 3.76 (s, 3H; 2-$OCH_3$), 4.06 (dd, $^3$J=4.3 and 11.7 Hz, 1H; 17aα-H), 6.97, 7.00 (2 s, 2H; 1-H, 4-H), 7.37 (s, 2H; $NH_2$), 7.82 (s, 2H; $NH_2$).

The invention claimed is:

1. A 2-Substituted D-homoestra-1,3,5(10)-trien-3-yl sulfamate of formula I (I)

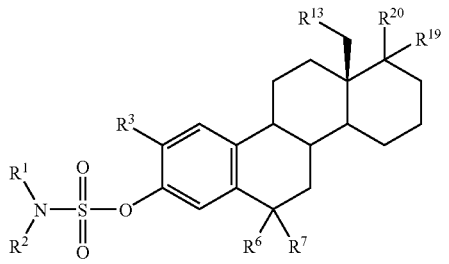

in which $R^1$ and $R^2$ are, independently of one another, a hydrogen atom, a methyl group, a $C_1$-$C_4$-acyl group or a benzoyl group, $R^3$ means a $C_1$-$C_5$-alkyl, a $C_1$-$C_5$-alkyloxy group or a radical —O—$C_nF_mH_o$, wherein n=1, 2, 3, 4, 5 or 6, m>1, and m+o=2n+1, $R^6$ and $R^7$, are, independently of one another, a hydrogen atom, a hydroxy group, an amino group or an $NHR^8$ group, wherein $R^8$ is an acetyl group, or $R^6$ and $R^7$ together are an oxime NOH, $R^{13}$ is a hydrogen atom or a methyl group, $R^{19}$ is a hydrogen atom or a fluorine atom, $R^{20}$ is a hydrogen atom or a fluorine atom or a hydroxy group or a $C_1$-$C_5$-alkyloxy group or $C_1$-$C_5$-alkyl group or a radical —$C_nF_mH_o$, wherein n=1, 2, 3, 4, 5 or 6, m>1 and m+o=2n+1, or a group $SO_2NR^1R^2$, or $R^{19}$ and $R^{20}$ together mean an oxygen atom, a methylene group, a difluoromethylene group or a monofluoromethylene group or an oxime $NOR^{21}$, wherein $R^{21}$ is a hydrogen atom or a $C_1$-$C_5$-alkyl group, or a pharmaceutically acceptable salt thereof.

2. A 2-Substituted D-homoestra-1,3,5(10)-trien-3-yl sulfamate according to claim 1, wherein $R^3$ represents a methyl, ethyl, methoxy, ethoxy or 2,2,2-trifluoroethoxy group.

3. A 2-Substituted D-homoestra-1,3,5(10)-trien-3-yl sulfamate according to claim 2, wherein $R^3$ represents a methoxy group.

4. A 2-Substituted D-homoestra-1,3,5(10)-trien-3-yl sulfamate according to claim 1, wherein $R^6$ and $R^7$ in each case represent a hydrogen atom.

5. A 2-Substituted D-homoestra-1,3,5(10)-trien-3-yl sulfamate according to claim 1, wherein $R^{19}$ represents a hydrogen atom.

6. A 2-Substituted D-homoestra-1,3,5(10)-trien-3-yl sulfamate according to claim 1, wherein $R^{20}$ represents a hydrogen atom or a hydroxy group.

7. A 2-Substituted D-homoestra-1,3,5(10)-trien-3-yl sulfamate according to claim 1, wherein $R^1$ represents a hydrogen atom.

8. A 2-Substituted D-homoestra-1,3,5(10)-trien-3-yl sulfamate according to claim 1, wherein $R^2$ represents a hydrogen atom or an acyl group.

9. A 2-Substituted D-homoestra-1,3,5(10)-trien-3-yl sulfamate according to claim 1, wherein $R^{13}$ represents a hydrogen atom or a methyl group.

10. A 2-Substituted D-homoestra-1,3,5(10)-trien-3-yl sulfamate[according to claim 1], which is 1) 2-Methoxy-17a-oxo-17a-homoestra-1,3,5(10)-trien-3-yl sulfamate
2) 2-Methoxy-17a-oxo-17a-homoestra-1,3,5(10)-trien-3-yl (N-acetyl)-sulfamate
3) 2-Methoxy-17a-homoestra-1,3,5(10)-trien-3-yl sulfamate
4) 2-Methoxy-17a-homoestra-1,3,5(10)-trien-3-yl (N-acetyl)-sulfamate
5) 2-Methoxy-6-oximino-17a-homoestra-1,3,5(10)-trien-3-yl sulfamate
6) 2-Methoxy-6-(O-methyloximino)-17a-homoestra-1,3,5(10)-trien-3-yl sulfamate
7) 6α-Hydroxy-2-methoxy-17a-homoestra-1,3,5(10)-trien-3-yl sulfamate
8) 6α-Acetylamino-2-methoxy-17a-homoestra-1,3,5(10)-trien-3-yl sulfamate
9) 2-Methoxy-6-oxo-17a-homoestra-1,3,5(10)-trien-3-yl sulfamate
10) 17aα-Hydroxy-2-methoxy-17a-homoestra-1,3,5(10)-trien-3-yl sulfamate
11) 17aβ-Hydroxy-2-methoxy-17a-homoestra-1,3,5(10)-trien-3-yl sulfamate
12) 2-Methoxy-17a-homoestra-1,3,5(10)-triene-3,17aβ-diyl bissulfamate
13) 2-Methoxy-17a-homoestra-1,3,5(10)-triene-3,17aβ-diyl bis-(N-acetyl)-sulfamate
14) 17a-Difluoro-2-methoxy-17a-homoestra-1,3,5(10)-trien-3-yl sulfamate
15) 17aα-Fluoro-2-methoxy-17a-homoestra-1,3,5(10)-trien-3-yl sulfamate
16) 17aβ-Fluoro-2-methoxy-17a-homoestra-1,3,5(10)-trien-3-yl sulfamate
17) 2-Methoxy-17a-oximino-17a-homoestra-1,3,5(10)-trien-3-yl sulfamate
18) 2-Methoxy-17a-(methyloximino)-17a-homoestra-1,3,5(10)-trien-3-yl sulfamate
19) 2,17aβ-Dimethoxy-17a-homoestra-1,3,5(10)-trien-3-yl sulfamate
20) 2,17aβ-Dimethoxy-17a-homoestra-1,3,5(10)-trien-3-yl (N-acetyl)-sulfamate
21) 17aβ-Ethoxy-2-methoxy-17a-homoestra-1,3,5(10)-trien-3-yl sulfamate
22) 17aβ-Ethoxy-2-methoxy-17a-homoestra-1,3,5(10)-trien-3-yl (N-acetyl)-sulfamate
23) 2-Methoxy-17aβ-(n-propoxy)-17a-homoestra-1,3,5(10)-trien-3-yl sulfamate
24) 2-Methoxy-17aβ-methyl-17a-homoestra-1,3,5(10)-trien-3-yl sulfamate
25) 17aβ-Difluoromethyl-2-methoxy-17a-homoestra-1,3,5(10)-trien-3-yl sulfamate
26) 17aβ-Fluoromethyl-2-methoxy-17a-homoestra-1,3,5(10)-trien-3-yl sulfamate
27) 17aβ-Ethyl-2-methoxy-17a-homoestra-1,3,5(10)-trien-3-yl sulfamate
28) 2-Methoxy-17a(20)-methylene-17a-homoestra-1,3,5(10)-trien-3-yl sulfamate
29) 17a(20)-Difluoromethylene-2-methoxy-17a-homoestra-1,3,5(10)-trien-3-yl sulfamate
30) 17a(20)-Fluoromethylene-2-methoxy-17a-homoestra-1,3,5(10)-trien-3-yl sulfamate
31) 2-Methoxy-17a-oxo-17a,18a-dihomoestra-1,3,5(10)-trien-3-yl sulfamate
32) 2-Methoxy-17a-oxo-17a,18a-dihomoestra-1,3,5(10)-trien-3-yl (N-acetyl)-sulfamate
33) 2-Methoxy-17a,18a-dihomoestra-1,3,5(10)-trien-3-yl sulfamate
34) 2-Methoxy-17a,18a-dihomoestra-1,3,5(10)-trien-3-yl (N-acetyl)-sulfamate
35) 2-Methoxy-6-oximino-17a,18a-dihomoestra-1,3,5(10)-trien-3-yl sulfamate
36) 2-Methoxy-6-(O-methyloximino)-17a,18a-dihomoestra-1,3,5(10)-trien-3-yl sulfamate
37) 6α-Hydroxy-2-methoxy-17a,18a-dihomoestra-1,3,5(10)-trien-3-yl sulfamate
38) 6α-Acetylamino-2-methoxy-17a,18a-dihomoestra-1,3,5(10)-trien-3-yl sulfamate
39) 17aβ-Hydroxy-2-methoxy-17a,18a-dihomoestra-1,3,5(10)-trien-3-yl sulfamate
40) 2-Methoxy-17a,18a-dihomoestra-1,3,5(10)-triene-3,17aβ-diyl bissulfamate
41) 2-Methoxy-17a,18a-dihomoestra-1,3,5(10)-triene-3,17aβ-diyl bis-(N-acetyl)-sulfamate
42) 17a-Difluoro-2-methoxy-17a,18a-dihomoestra-1,3,5(10)-trien-3-yl sulfamate
43) 17aα-Fluoro-2-methoxy-17a,18a-dihomoestra-1,3,5(10)-trien-3-yl sulfamate
44) 17aβ-Fluoro-2-methoxy-17a,18a-dihomoestra-1,3,5(10)-trien-3-yl sulfamate
45) 2-Methoxy-17a-oximino-17a,18a-dihomoestra-1,3,5(10)-trien-3-yl sulfamate
46) 2-Methoxy-17a-(methyloximino)-17a,18a-dihomoestra-1,3,5(10)-trien-3-yl sulfamate
47) 2,17aβ-Dimethoxy-17a,18a-dihomoestra-1,3,5(10)-trien-3-yl sulfamate
48) 17aβ-Ethoxy-2-methoxy-17a,18a-dihomoestra-1,3,5(10)-trien-3-yl sulfamate
49) 2-Methoxy-17aβ-(n-propoxy)-17a,18a-dihomoestra-1,3,5(10)-trien-3-yl sulfamate
50) 2-Methoxy-17aβ-methyl-17a,18a-dihomoestra-1,3,5(10)-trien-3-yl sulfamate
51) 17aβ-Difluoromethyl-2-methoxy-17a,18a-dihomoestra-1,3,5(10)-trien-3-yl sulfamate
52) 17aβ-Fluoromethyl-2-methoxy-17a,18a-dihomoestra-1,3,5(10)-trien-3-yl sulfamate
53) 17aβ-Ethyl-2-methoxy-17a,18a-dihomoestra-1,3,5(10)-trien-3-yl sulfamate
54) 2-Methoxy-17a(20)-methylene-17a,18a-dihomoestra-1,3,5(10)-trien-3-yl sulfamate
55) 17a(20)-Difluoromethylene-2-methoxy-17a,18a-dihomoestra-1,3,5(10)-trien-3-yl sulfamate
56) 17a(20)-Fluoromethylene-2-methoxy-17a,18a-dihomoestra-1,3,5(10)-trien-3-yl sulfamate
57) 2-Ethyl-17a-oxo-17a-homoestra-1,3,5(10)-trien-3-yl sulfamate
58) 2-Ethyl-17a-oxo-17a-homoestra-1,3,5(10)-trien-3-yl (N-acetyl)-sulfamate
59) 2-Ethyl-17a-homoestra-1,3,5(10)-trien-3-yl sulfamate
60) 2-Ethyl-17a-homoestra-1,3,5(10)-trien-3-yl (N-acetyl)-sulfamate
61) 2-Ethyl-17aβ-hydroxy-17a-homoestra-1,3,5(10)-trien-3-yl sulfamate 62) 2-Ethyl-17a-homoestra-1,3,5(10)-triene-3,17aβ-diyl bissulfamate 63) 2-Ethyl-17a-homoestra-1,3,5(10)-triene-3,17aβ-diyl bis-(N-acetyl)-sulfamate 64) 2-Ethyl-17aβ-methoxy-17a-homoestra-1,3,5(10)-trien-3-yl sulfamate or 65) 2-Ethyl-17aβ-ethoxy-17a-homoestra-1,3,5(10)-trien-3-yl sulfamate.

11. A pharmaceutical composition comprising at least one compound of formula I according to claim 1 and a pharmaceutically compatible carrier and optionally one or more additional active ingredients.

12. A method of preparing a pharmaceutical composition according to claim 11, comprising bringing together into a composition a 2-substituted D-homoestra-1,3,5(10)-trien-3-yl sulfamate and a pharmaceutically acceptable carrier.

13. A method for treating a tumor disease that can be positively influenced by the inhibition of tubulin polymerization, wherein said tumor disease is selected from the group consisting of breast cancer, prostate cancer, colon cancer, non-small-cell-lung cancer and primary dermal microvascular endothelial cell proliferation comprising administering to a subject in need thereof an effective amount of a 2-Substituted D-homoestra-1,3,5(10)-trien-3-yl sulfamate according to claim 1.

14. A method according to claim 13, further comprising administering at least one additional active ingredient.

15. A method according to claim 13, wherein the disease treated is a disease of a male or female gonad, of a male or female sex organ, or of a mammary gland, that can be positively influenced by the inhibition of tubulin polymerization and wherein said disease is selected from the group consisting of breast cancer, prostate cancer, colon cancer, non-small-cell-lung cancer and primary dermal microvascular endothelial cell proliferation.

16. A method according to claim 13, which is for treating breast cancer.

17. A method according to claim 13, which is for treating prostate cancer.

18. A method according to claim 13, which is for treating colon cancer, non-small-cell-lung cancer, or primary dermal microvascular endothelial cell proliferation.

19. A method for treating breast cancer comprising administering to a subject in need thereof an effective amount of a 2-Substituted D-homoestra-1,3,5(10)-trien-3-yl sulfamate according to claim 1.

20. A method for treating prostate cancer comprising administering to a subject in need thereof an effective amount of a 2-Substituted D-homoestra-1,3,5(10)-trien-3-yl sulfamate according to claim 1.

21. A method for treating colon cancer comprising administering to a subject in need thereof an effective amount of a 2-Substituted D-homoestra-1,3,5(10)-trien-3-yl sulfamate according to claim 1.

22. A method for treating non-small-cell-lung cancer comprising administering to a subject in need thereof an effective amount of a 2-Substituted D-homoestra-1,3,5(10)-trien-3-yl sulfamate according to claim 1.

23. A method for treating primary dermal microvascular endothelial cell proliferation comprising administering to a subject in need thereof an effective amount of a 2-Substituted D-homoestra-1,3,5(10)-trien-3-yl sulfamate according to claim 1.

24. A method for treating breast cancer, prostate cancer, colon cancer, non-small-cell-lung cancer, or primary dermal microvascular endothelial cell proliferation comprising administering to a subject in need thereof an effective amount of a 2-Substituted D-homoestra-1,3,5(10)-trien-3-yl sulfamate according to claim 10.

*25. A 2-Substituted D-homoestra-1,3,5(10)-trien-3-yl sulfamate according to claim 1, wherein* $R^{20}$ *is a hydrogen atom or a fluorine atom or a hydroxy group or* $C_1$-$C_5$-*alkyloxy group or a* $C_1$-$C_5$-*alkyl group or radical* $—C_nF_mH_o$.

* * * * *